US006640371B2

(12) United States Patent
Green et al.

(10) Patent No.: US 6,640,371 B2
(45) Date of Patent: Nov. 4, 2003

(54) TOPICAL INCORPORATION OF SOLID ANTIMICROBIAL COMPOUNDS ON YARN SURFACES THROUGH HIGH PRESSURE

(75) Inventors: David E. Green, Simpsonville, SC (US); Leland G. Close, Jr., Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 10/146,642

(22) Filed: May 15, 2002

(65) Prior Publication Data

US 2002/0127402 A1 Sep. 12, 2002

Related U.S. Application Data

(62) Division of application No. 09/586,081, filed on Jun. 2, 2000.

(51) Int. Cl.[7] ............................ D06B 3/09; D06M 11/84
(52) U.S. Cl. ........................ 8/155; 8/115.6; 427/389.9
(58) Field of Search ............................ 8/494, 495, 155, 8/115.6; 427/389.9

(56) References Cited

U.S. PATENT DOCUMENTS

| | | | |
|---|---|---|---|
| 3,377,249 A | 4/1968 | Marco | 570/169 |
| 3,540,835 A | 11/1970 | Marco | 570/169 |
| 3,563,795 A | 2/1971 | Williams et al. | 117/139.4 |
| 3,574,620 A | 4/1971 | Tesoro et al. | 117/62.1 |
| 3,598,641 A | 8/1971 | Miller et al. | 117/138.8 |
| 3,620,826 A | 11/1971 | Machell | 117/139.5 |
| 3,625,754 A | 12/1971 | Dunn | 117/138.8 |
| 3,632,420 A | 1/1972 | Kuhn | 117/138.8 |
| 3,650,801 A | 3/1972 | Hinton, Jr. et al. | 117/47 |
| 3,652,212 A | 3/1972 | Machell | 8/115.5 |
| 3,660,010 A | 5/1972 | Georgoudis et al. | 8/115.6 |
| 3,676,052 A | 7/1972 | Harper et al. | 8/115.6 |
| 3,690,942 A | 9/1972 | Vandermass et al. | 117/138.8 |
| 3,897,206 A | 7/1975 | Kearney | 8/120 |
| 3,981,807 A | 9/1976 | Raynolds | 252/8.8 |
| 4,014,857 A | 3/1977 | Schmoyer | 260/67.7 |
| 4,068,035 A | 1/1978 | Violland et al. | 428/279 |
| 4,073,993 A | 2/1978 | Lark | 428/261 |
| 4,090,844 A | 5/1978 | Rowland | 8/120 |
| 4,131,550 A | 12/1978 | Marco | 252/8.6 |
| 4,164,392 A | 8/1979 | Hauser et al. | 8/18 |
| 4,168,954 A | 9/1979 | Marco | 8/18 |
| 4,207,071 A | 6/1980 | Lipowitz et al. | 8/115.6 |
| 4,290,765 A | 9/1981 | Sandler | 8/115.6 |
| 4,369,035 A * | 1/1983 | Karrer et al. | |
| 4,427,557 A | 1/1984 | Stockburger | 252/8.7 |
| 4,842,932 A * | 6/1989 | Burton | |
| 5,180,585 A * | 1/1993 | Jacobson et al. | |
| 6,454,813 B1 * | 9/2002 | Chan | |

* cited by examiner

*Primary Examiner*—Margaret Einsmann
(74) *Attorney, Agent, or Firm*—Terry T. Moyer; William S. Parks

(57) ABSTRACT

Durable antimicrobial treatments for high pressure treatments (such as package dyeing) for specific dyed yarns for further incorporation within textile fabrics are provided. Such treatments preferably comprise silver ions, particularly as constituents of inorganic metal salts or zeolites. This particular treatment requires the presence of a resin binder as a component of the dye bath formulation admixed with the silver-ion antimicrobial compound, the formulation then forced through a target yarn spool in order to provide a finish over substantially all of the target yarn. The yarn may then be knit, woven, pressed, laid-in, etc., into a textile fabric exhibiting antimicrobial properties. Such a treatment has been found to be extremely durable on such substrates; after a substantial number of standard launderings and dryings, the treatment does not wear away in any appreciable amount and thus the substrate retains its antimicrobial activity. The particular treatment method, as well as the treated textile fabrics, are also encompassed within this invention.

8 Claims, No Drawings

TOPICAL INCORPORATION OF SOLID ANTIMICROBIAL COMPOUNDS ON YARN SURFACES THROUGH HIGH PRESSURE

CROSS REFERENCE TO RELATED APPLICATIONS

This application is a divisional of co-pending application Ser. No. 09/586,081, filed on Jun. 2, 2000 pending.

FIELD OF THE INVENTION

This invention relates to high pressure antimicrobial treatments for specific yarns (such as package dyeing) for further incorporation within textile fabrics. Such treatments preferably comprise silver ions, particularly as constituents of inorganic metal salts or zeolites. In order to impart wash durability to the inventive package dyed treatment, this preferred treatment generally requires the presence of a resin binder as a component of the dye bath formulation admixed with the silver-ion antimicrobial compound, the formulation then forced through a target yarn spool in order to provide a finish over substantially all of the target yarn. The yarn may then be knit, woven, pressed, laid-in, etc., into a textile fabric exhibiting antimicrobial properties. Alternatively, the binder resin may be applied only after treatment and textile formation. Such a treatment has been found to be extremely durable on such substrates; after a substantial number of standard launderings and dryings, the treatment does not wear away in any appreciable amount and thus the substrate retains its antimicrobial activity. The particular treatment method, as well as the treated textile fabrics, are also encompassed within this invention.

DISCUSSION OF THE PRIOR ART

There has been a great deal of attention in recent years given to the hazards of bacterial contamination from potential everyday exposure. Noteworthy examples of such concern include the fatal consequences of food poisoning due to certain strains of *Eschericia coli* being found within undercooked beef in fast food restaurants; Salmonella contamination causing sicknesses from undercooked and unwashed poultry food products; and illnesses and skin infections attributed to *Staphylococcus aureus, Klebsiella pneumoniae,* yeast, and other unicellular organisms. With such an increased consumer interest in this area, manufacturers have begun introducing antimicrobial agents within various household products and articles. For instance, certain brands of polypropylene cutting boards, liquid soaps, etc., all contain antimicrobial compounds. The most popular antimicrobial for such articles is triclosan. Although the incorporation of such a compound within liquid or polymeric media has been relatively simple, other substrates, including the surfaces of textiles and fibers, have proven less accessible. There is a long-felt need to provide effective, durable, and long-lasting antimicrobial characteristics for textile surfaces, in particular on apparel fabrics, and on film surfaces. Such proposed applications have been extremely difficult to accomplish with triclosan, particularly when wash durability is a necessity (triclosan easily washes off any such surfaces). Furthermore, although triclosan has proven effective as an antimicrobial compound, the presence of chlorines and chlorides within such a compound causes skin irritation which makes the utilization of such with fibers, films, and textile fabrics for apparel uses highly undesirable. Furthermore, there are commercially available textile products comprising acrylic and/or acetate fibers co-extruded with triclosan (for example Celanese markets such acetate fabrics under the name Microsafe™ and Acordis markets such acrylic fibers, under the tradename Amicor™). However, such an application is limited to those types of fibers; it does not work specifically for and within polyester, polyamide, cotton, spandex, etc., fabrics. Furthermore, this co-extrusion procedure is very expensive.

Silver-containing inorganic microbiocides have recently been developed and utilized as antimicrobial agents on and within a plethora of different substrates and surfaces. In particular, such microbiocides have been adapted for incorporation within melt spun synthetic fibers, as taught within Japanese unexamined Patent Application No. H11-124729, in order to provide certain fabrics which selectively and inherently exhibit antimicrobial characteristics. Furthermore, attempts have been made to apply such specific microbiocides on the surfaces of fabrics and yarns with little success from a durability standpoint. A topical treatment with such compounds has never been successfully applied as a durable finish or coating on a fabric or yarn substrate. Although such silver-based agents provide excellent, durable, antimicrobial properties, to date such is the sole manner available within the prior art of providing a long-lasting, wash-resistant, silver-based antimicrobial textile. However, such melt spun fibers are expensive to make due to the large amount of silver-based compound required to provide sufficient antimicrobial activity in relation to the migratory characteristics of such a compound within the fiber itself to its surface. A topical coating is also desirable for textile and film applications, particularly after finishing of the target fabric or film. Such a topical procedure permits treatment of a fabric's individual fibers prior to or after weaving, knitting, and the like, in order to provide greater versatility to the target yarn without altering its physical characteristics. Such a coating, however, must prove to be wash durable, particularly for apparel fabrics, in order to be functionally acceptable. Furthermore, in order to avoid certain problems, it is highly desirable for such a metallized treatment to be electrically non-conductive on the target fabric, yarn, and/or film surface. With the presence of metals and metal ions, such a wash durable, non-electrically conductive coating has not been available in the past. Such an improvement would thus provide an important advancement within the textile, yarn, and film art. Although antimicrobial activity is one desired characteristic of the inventive metal-treated fabric, yarn, or film, this is not a required property of the inventive article. Odor-reduction, heat retention, distinct coloriations, reduced discolorations, improved yarn and/or fabric strength, resistance to sharp edges, etc., are all either individual or aggregate properties which may be accorded the user of such an inventive treated yarn, fabric, or film.

DESCRIPTION OF THE INVENTION

It is thus an object of the invention to provide a simple manner of effectively treating a yarn in a package dye method with a wash-durable antimicrobial silver-ion containing treatment. Another object of the invention is to provide an aesthetically pleasing metal-ion-treated textile which is wash durable, non-yellowing, non-irritating to skin, and which provides antimicrobial properties.

Accordingly, this invention encompasses a yarn treated with a wash-durable antimicrobial finish, wherein said yarn is treated through a high pressure procedure involving the following sequential steps:

(a) providing a spool of yarn;
(b) providing a formulation comprising a dispersion of a solid antimicrobial compound and optionally a binder material;

(c) placing said spool of yarn within said dye bath formulation; and (d) pumping said formulation through said spool of yarn at a pressure of between about 0.1 and 100 pounds per square inch for from about 5 seconds to about 5 hours at a temperature in the range from about 25° to about 325° C. Also encompassed within this invention is a process for producing a yarn exhibiting antimicrobial characteristics comprising the steps of (a) providing a spool of yarn;

(b) providing a formulation comprising a dispersion of a solid antimicrobial compound;

(c) placing said spool of yarn within said dye bath formulation;

(d) pumping said dye bath formulation through said spool of yarn at a pressure of between about 0.1 and 100 pounds per square inch for from about 5 seconds to about 5 hours at a temperature in the range from about 25° to about 325° C.;

(e) combining said yarn with a plurality of other yarns to form a textile fabric; and (f) coating at least a portion of said yarn within the textile fabric of step "e" with a binder resin. The resultant yarn can then be utilized as one component of a textile fabric to provide antimicrobial characteristics at a level of at least 99.0% (log kill rate of at least 3.0) for *Klebsiella pneumoniae* and other microbes (such as, for example, *Staphylococcus aureus*). By itself, the topical solid compound treatment provides a durable finish on the target yarn. When incorporated within a fabric (through weaving, knitting, adhering, placing, insetting, and the like), the finish provides a *K. pneumoniae* log kill rate in excess of 1.5, preferably in excess of 2.0, still more preferably in excess of 3.0, even more preferably in excess of 3.4, and most preferably in excess of 3.6, for the target fabric after 5 standard launderings performed in accordance with the wash procedure as part of AATCC Test Method 130-1981. When admixed or coated with a binder material, the inventive treatment exhibits the same high *K. pneumnoniae* log kill rates with simiultaneous long-lasting wash durability in excess of 10 standard launderings performed in accordance with the wash procedure as part of AATCC Test Method 130-1981. Thus, even without the binder material present, surprisingly the inventive package dyed yarn (and textiles made therefrom) exhibits high durable antimicrobial activity. The wash durability test noted above is standard and, as will be well appreciated by one of ordinary skill in this art, is not intended to be a required or limitation within this invention. Such a test method merely provides a standard which, upon 5 or 10 washes in accordance with such, the inventive treated substrate will not lose an appreciable amount of its antimicrobial finish.

Nowhere within the prior art has such a specific treated substrate or method of making thereof been disclosed, utilized, or fairly suggested. The closest art is a product marketed under the tradename X-STATIC® which is a fabric article electrolessly plated with a silver coating. Such a fabric is highly electrically conductive and is utilized for static charge dissipation. Also, the coating alternatively exists as a removable silver powder finish on a variety of surfaces. The aforementioned Japanese patent publication to Kuraray is limited to fibers within which a silver-based compound has been incorporated through melt spun fiber techniques. Nowhere has such a wash-durable topical high pressure treatment as now claimed been mentioned or alluded to.

Any yarn may be utilized as the substrate within this application. Thus, natural (cotton, wool, ramie, hemp, linen, and the like), synthetic (polyesters, polyamides, polyolefins, polyaramids, acetates, rayon, acrylics, and the like), or inorganic fibers (such as fiberglass, boron-derivative fibers, and the like) may constitute the target yarn, either alone or in any combinations or mixtures of synthetics, naturals, or blends or both types. As for the synthetic types, for instance, and without intending any limitations therein, polyolefins, such as polyethylene, polypropylene, and polybutylene, halogenated polymers, such as polyvinyl chloride, polyesters, such as polyethylene terephthalate, polyester/ polyethers, polyamides, such as nylon 6 and nylon 6,6, polyurethanes, as well as homopolymers, copolymers; or terpolymers in any combination of such monomers, and the like, may be utilized within this invention. Nylon 6, Nylon 6,6, polypropylene, and polyethylene terephthalate (a polyester) are particularly preferred. The selected fiber or yarn may be of any denier, may be of multi- or mono-filament, may be false-twisted or twisted, or may incorporate multiple denier fibers or filaments into one single yarn through twisting, melting, and the like. Furthermore, the yarn may be dyed or colored to provide other aesthetic features for the end user with any type of colorant, such as, for example, poly(oxyalkylenated) colorants, as well as pigments, dyes, tints, and the like. Other additives may also be present on and/or within the target fabric or yarn, including antistatic agents, brightening compounds, nucleating agents, antioxidants, UV stabilizers, fillers, permanent press finishes, softeners, lubricants, curing accelerators, and the like. Particularly desired as optional and supplemental finishes to the inventive yarns or fabrics made therefrom are soil release agents which improve the wettability and washability of the fabric. Preferred soil release agents include those which provide hydrophilicity to the surface of polyester. With such a modified surface, again, the fabric imparts improved comfort to a wearer by wicking moisture. The preferred soil release agents contemplated within this invention may be found in U.S. Pat. Nos. 3,377,249; 3,540,835; 3,563,795; 3,574,620; 3,598,641; 3,620,826; 3,632,420; 3,649,165; 3,650,801; 3,652,212; 3,660,010; 3,676,052; 3,690,942; 3,897,206; 3,981,807; 3,625,754; 4,014,857; 4,073,993; 4,090,844; 4,131,550; 4,164,392; 4,168,954; 4,207,071; 4,290,765; 4,068,035; 4,427,557; and 4,937,277. These patents are accordingly incorporated herein by reference. Additionally, other potential additives and/or finishes may include water repellent fluorocarbons and their derivatives, silicones, waxes, and other similar water-proofing materials.

The particular treatment must comprise at least one type of a solid antimicrobial compound, preferably metal-based compounds and/or ion-exchange compounds, and most preferably silver-based antimicrobial compounds, or mixtures thereof of different types. The term silver-based compounds encompasses compounds which are silver-based ion-exchange resins, zeolites, or, possibly substituted glass compounds (which release the particular metal ion bonded thereto upon the presence of other anionic species). The preferred metal-ion containing compound for this invention is an antimicrobial silver zirconium phosphate available from Milliken & Company, under the tradename ALPHASAN®. Other potentially preferred silver-containing antimicrobials in this invention is a silver-substituted zeolite available from Sinanen under the tradename ZEOMIC® AJ, or a silver-substituted glass available from Ishizuka Glass under the tradename IONPURE®, may be utilized either in addition to or as a substitute for the preferred species. Such compounds actually appear to provide silver ion as the antimicrobially active component. Although such silver-ion producing compounds are preferred, it is to be well understood that other solid compounds, such as transition metal particles, salts, oxides, zeolites, ion-exchange compounds, and the like, may be utilized as part or all of the inventive yarn's solid antimicrobial component. The term transition metal is intended to encompass any or all of the standard, well known, transition metals, including wihout limitation silver, gold, platinum, manganese, magnesium, zinc, copper, iron, and the like. Again, silver and zinc are preferred with silver most preferred. Generally, such a solid antimicrobial compound is added in an amount of from about 0.01 to 40% by total weight of the particular treatment composition; more preferably from about 0.05 to about 30%; and most preferably from about 0.1 to about 30% (most preferably about 30% owf). Preferably the solid antimicrobial compound add-on weight is from about 0.01 to about 5% owf, preferably from about 0.05 to about 3.0% owf, more preferably from about 0.1 to about 2% owf, and most preferably about 1.0% owf. The treatment itself, including any optional binders, adherents, thickeners, and the like, is added to the substrate in an amount of from about 0.01 to about 10% owf The binder material, which, although optional, does provide highly beneficial durability for the inventive yarns, is preferably selected from a permanent press type resin and an acrylic type resin. Such resins provide washfastness by adhering silver to the target yarn and/or fabric surface. Such binding agents must not be cationic or strongly anionic in nature; slightly anionic materials are acceptable. In general, such binding agents thus must exhibit adhesion to the target substrate as well as the target antimicrobial solids, and must also act to retain such solids on the target substrate surface. More particular classes of such binding agents include acrylic based materials (such as, without limitation, Rhoplex® TR3082 from Rohm & Haas), nonionic permanent press agents (a term well known in the art, compounds of which include, without limitation, Permafresh®, available from Sequa). Such binders may be applied within the high pressure procedure itself, or topically applied subsequent to fabric formation with the inventive yarns. In any event, the amount applied should roughly be from about 0.01 to about 10% owf, preferably from about 0.05 to about 5% owf, more preferably from about 2 to about 3% owf, and most preferably about 2.5% owf.

Textile fabrics may be produced with the same yarns discussed above, including any blends thereof. Such fabrics may be of any standard construction, including knit, woven, or nonwoven forms. The inventive fabrics may be utilized in any suitable application, including, without limitation, apparel, upholstery, bedding, wiping cloths, towels, gloves, rugs, floor mats, drapery, napery, bar runners, textile bags, awnings, vehicle covers, boat covers, tents, and the like. The inventive fabric may also be coated, printed, colored, dyed, and the like.

The high pressure procedure necessary for providing the antimicrobial solid application on the surface of the target yarns must be sufficient to permit penetration of the solid compounds into the actual yarn structure. A high temperature may be desired to permit "opening" of the fiber structure to facilitate such solids introduction within a solid yarn. In general, the high pressure conditions must be from about 0.1 and 100 pounds per square inch with an exposure time of from about 5 seconds to about 5 hours at a temperature in the range from about 25° to about 325° C. Such conditions are most readily provided within a jet dye, closed vessel system, and appears to work most readily for package dyed yarns. The type of fiber is consequential only to the extent that certain temperatures permit easier penetration within certain fibers. Thus, natural fibers (such as cotton) require relatively low temperatures to "open" of the cellulosic structure; nylon requires a much higher temperature (to exceed its glass transition temperature, typically) to provide the most effective antimicrobial characteristics. For the most part, the high pressure actually appears to force the solid particles into the yarns; surprisingly, such solid—solid interaction works to retain a substantial amount of the solid antimicrobial, even after washing. Preferably, however, a binder agent is added to aid in solid particle retention since such solid particles will most likely exhibit a desire to become detached from the yarn over time.

The inventive procedure was developed "through an initial attempt at understanding the ability of such metal-ion containing compounds to attach to a fabric surface. Thus, a sample of ALPHASAN® was first exhausted from a dye bath on to a target polyester fabric surface. The fabric was then tested for antimicrobial characteristics at different locations on the fabric surface. The fabric exhibited excellent log kill rate characteristics; however, upon washing in a standard laundry method (AATCC Test Method 103-1981, for instance), the antimicrobial activity was drastically reduced. Such promising initial results led to the inventive washdurable antimicrobial treatment wherein the desired metal-ion containing compound would be forceably introduced within a the surface of a target yarn through a high pressure treatment with a formulation comprising a dispersion of the desired solid antimicrobial compound and optionally a binder material. More succinctly, and preferably, the desired solid antimicrobial compound was admixed with a binder resin within a dye bath formulation and forced through a spool of target yarn during a package dye procedure. This specific procedure yielded an excellent longlasting, washdurable, and antimicrobially effective treatment on the target yarns. The knit fabrics including these yarns thus exhibited both excellent antimicrobial results and washdurability, even after as many as ten standard laundering procedures. Without the binder resin, the target fabrics still exhibited surprisingly high levels of antimicrobial effective and durability.

The preferred embodiments of these alternatives fabric treatments are discussed in greater detail below.

DESCRIPTION OF THE PREFERRED EMBODIMENTS

Examples of particularly preferred methods and articles compounds within the scope of the present invention are set forth below.

EXAMPLE 1

Several spools of 150 denier polyester multifilament yarn were placed within a sealed dye bath. The dye bath liquor contained 1.0% owf of active ALPHASAN®, 0.5% by weight of nonionic leveler 528 (butyl benzoate, available from Milliken & Company), and the balance water. After sealing of the chamber, the pump was activated at a pressure of 60 psi at a temperature of about 280° F. The pump remained activated for about 60 minutes. The resultant spools of yarn were then utilized in a knitting operation to produce a sock. Three different discrete areas of the sock were tested for log kill rates for *K. pneumoniae* after different numbers of launderings. The colorations of the sock remained virtually the same after such repeated launderings. The log kill results are tabulated below:

TABLE 1

Log Kill Rates On The Knit Fabrics (Binder-Free)

| Number of Washes | Log Kill Rate for *K. pneumoniae* |
|---|---|
| 0 | 4.43 |
| 5 | 4.13 |

The knit fabric thus retained a substantial amount of its ALPHASAN® finish applied during the package dyeing process for an extremely long duration.

EXAMPLE 2

Several spools of 150 denier multifilament polyester yarn were placed within a sealed dye bath. The dye bath liquor contained 1.0% owf of active ALPHASAN®, 0.5% owf nonionic leveler 528, 2.0% owf of Rhoplex® TR3082 (an acrylic-based slightly anionic binding agent), and the balance water. After sealing of the chamber, the pump was activated at a pressure of 60 psi at a temperature of about 280° F. The pump remained activated for about 60 minutes. The resultant spools of yarn were then utilized in a knitting operation to produce a sock. Three different discrete areas of the sock were tested for log kill rates for *K. pneumoniae* after different numbers of launderings. The colorations of the sock remained virtually the same after such repeated launderings. The log kill results are tabulated below:

TABLE 2

Log Kill Rates On The Knit Fabrics (With Acrylic Binder)

| Number of Washes | Log Kill Rate for *K. pneumoniae* |
|---|---|
| 0 | 4.43 |
| 5 | 4.20 |
| 10 | 4.03 |

The knit fabric thus retained a substantial amount of its ALPHASAN® finish applied during the package dyeing process for an extremely long duration.

EXAMPLE 3

Several spools of 150 denier multifilament polyester yarn were placed within a sealed dye bath. The dye bath liquor contained 1.0% owf of active ALPHASAN®, 0.5% owf of nonionic leveler 528, and the balance water. After sealing of the chamber, the pump was activated at a pressure of 60 psi at a temperature of about 280° F. The pump remained activated for about 60 minutes. The resultant spools of yarn were then utilized in a knitting operation to produce a sock. A permanent press binding agent (2.0% owf of Permafresh®, available from Sequa) was then padded on the entire sock. After drying, three different discrete areas of the sock were tested for log kill rates for *K. pneumoniae* after different numbers of launderings. The colorations of the sock remained virtually the same after such repeated launderings. The log kill results are tabulated below:

TABLE 3

Log Kill Rates On The Knit Fabrics (With Permanent Press Binder)

| Number of Washes | Log Kill Rate for *K. pneumoniae* |
|---|---|
| 0 | 4.43 |
| 5 | 4.42 |
| 10 | 3.85 |

The knit fabric thus retained a substantial amount of its ALPHASAN® finish applied during the package dyeing process for an extremely long duration.

There are, of course, many alternative embodiments and modifications of the present invention which are intended to be included within the spirit and scope of the following claims.

What I claim is:

1. A process for producing a yarn exhibiting antimicrobial characteristics comprising the steps of
    (a) providing a spool of yarn;
    (b) providing a formulation comprising a dispersion of solid silver-ion containing antimicrobial compounds and optionally a binder material;
    (c) placing said spool of yarn within said dispersion of step "b";
    (d) pumping said dispersion of step "b" through said spool of yarn at a pressure of between about 0.1 and 100 pounds per square inch for from about 5 seconds to about 5 hours at a temperature in the range from about 25° to about 325° C. in order to attach at least one of said solid silver-ion containing antimicrobial compounds within said dispersion to said yarn.

2. The process of claim 1 wherein said solid silver-ion containing antimicrobial compound is selected from the group consisting of silver-containing ion exchange resins, silver-containing zeolites, silver-containing glass, and any mixtures thereof.

3. The process of claim 2 wherein said silver-ion containing antimicrobial compound is a silver zirconium phosphate ion exchange resin.

4. The process of claim 1 wherein said binder material of said dispersion of step "b" is present.

5. A process for producing a fabric exhibiting antimicrobial characteristics comprising the steps of
    (a) providing a spool of yarn;
    (b) providing a formulation comprising a dispersion of solid silver-ion containing antimicrobial compounds and optionally a binder material;
    (c) placing said spool of yarn within said dispersion of step "b";
    (d) pumping said dispersion of step "b" through said spool of yarn at a pressure of between about 0.1 and 100 pounds per square inch for from about 5 seconds to about 5 hours at a temperature in the range from about 25° to about 325° C. in order to attach at least one of said solid silver-ion containing antimicrobial compounds within said dispersion to said yarn;
    (e) combining said yarn with a plurality of other yarns to form a textile fabric; and (f) coating at least a portion of said yarn within the textile fabric of step "e" with a binder resin.

6. The process of claim 5 wherein said solid silver-ion containing antimicrobial compound is selected from the group consisting of silver-containing ion exchange resins, silver-containing zeolites, silver-containing glass, and any mixtures thereof.

7. The process of claim 6 wherein said silver-ion containing antimicrobial compound is a silver zirconium phosphate ion exchange resin.

8. The process of claim 5 wherein said binder material of said dispersion of step "b" is present.

* * * * *

UNITED STATES PATENT AND TRADEMARK OFFICE
CERTIFICATE OF CORRECTION

PATENT NO. : 6,640,371 B2
DATED : November 4, 2003
INVENTOR(S) : David E. Green and Leland G. Close, Jr.

It is certified that error appears in the above-identified patent and that said Letters Patent is hereby corrected as shown below:

<u>Title page,</u>
Item [54], Title, insert the word -- METHODS -- after the word "PRESSURE".

Signed and Sealed this

Third Day of May, 2005

JON W. DUDAS
*Director of the United States Patent and Trademark Office*